United States Patent [19]

Kinzy

[11] Patent Number: 5,319,077

[45] Date of Patent: Jun. 7, 1994

[54] PROCESS FOR THE PREPARATION OF SUGAR EPITOPES

[75] Inventor: Willy Kinzy, Inzlingen, Fed. Rep. of Germany

[73] Assignee: Merck Patent Gesellschaft Mit Beschränkter Haftung, Darmstadt, Fed. Rep. of Germany

[21] Appl. No.: 896,865

[22] Filed: Jun. 12, 1992

[30] Foreign Application Priority Data

Jun. 13, 1991 [DE] Fed. Rep. of Germany ....... 4119472

[51] Int. Cl.$^5$ .......................................... C07H 15/18
[52] U.S. Cl. .............................. 536/17.2; 536/123.1; 536/18.6
[58] Field of Search ..................... 536/17.2, 18.6, 123.1

[56] References Cited

PUBLICATIONS

Garegg, Per J. et al., Carbohydrate Research, 136 (1985), pp. 207–213.

Primary Examiner—Herbert J. Lilling
Attorney, Agent, or Firm—Millen, White, Zelano & Branigan

[57] ABSTRACT

The invention relates to a new process for the stereoselective preparation of Gal-$\alpha$(1–3)/Gal-$\beta$(1–4)/GlcNac trisaccharides of the formula

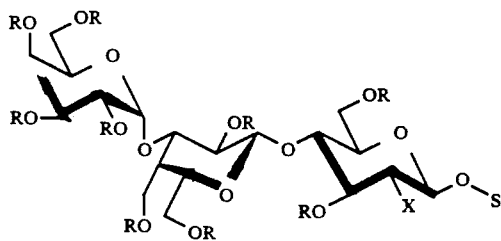

and of $\beta$(1–3)-linked oligolactosamines of the formula

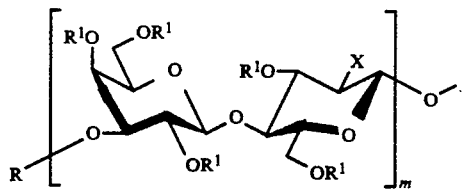

via partially alkylated glycals of the formula

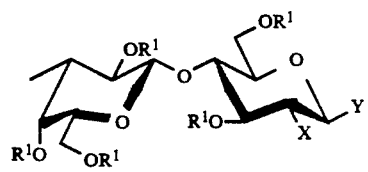

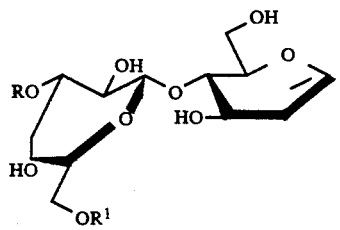

and other new intermediate products, wherein, depending on the formula, R is H, R'CH$_2$—, or allyl,
R$^1$ is H, R'CH$_2$—, allyl or R'CO—,
R' is H, C$_1$ to C$_3$-alkyl or (un)substituted phenyl,
Sp is a spacer, preferably of the formula —(CH$_2$)$_n$—COOR",
R" is alkyl having 1 to 4 C atoms,
X is N$_3$ or —NHCOCH$_3$,
X is N$_3$ or —NHCOCH$_3$,
Y is $\beta$-OSiR$_2^3$ or $\alpha$-OC(=NH)CCl$_3$,
R$^2$ is C$_1$ or C$_4$-alkyl or phenyl and
m and n are integers from 1 to 4 or 4 to 12 respectively.

15 Claims, No Drawings

PROCESS FOR THE PREPARATION OF SUGAR EPITOPES

SUMMARY OF THE INVENTION

The invention relates to a new process for the stereoselective preparation of Gal-α(1–3)/Gal-β(1–4)/Glc-Nac trisaccharides and of β(1–3)-linked oligolactosamines via partially alkylated glycals.

The invention specifically relates to a process for the stereoselective preparation of trisaccharides having the α(1–3),β(1–4)-configuration, of the formula I

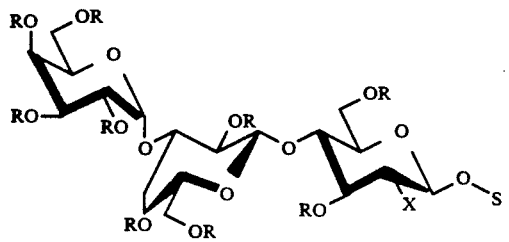

wherein
R is H or R'CH$_2$—,
R' is H or alkyl having 1 to 3 C atoms or phenyl which is unsubstituted or substituted by halogen, OH, alkyl or O-alkyl,
S is a spacer and
X is N$_3$ or —NHCOCH$_3$,
from lactose, characterized in that
i. lactose is converted into D-lactal;
ii. D-lactal is partially alkylated to give the new lactal derivatives of the formula II

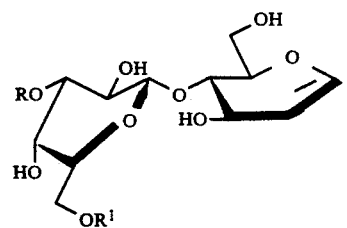

wherein
R—is R'CH$_2$—or —CH$_2$—CH=CH$_2$,
R$^1$ is H, R'CH$_2$—, CH$_2$—CH=CH$_2$ or R'—C(O)—and
R' is H, alkyl having 1 to 3 C atoms or phenyl which is unsubstituted or substituted by halogen, OH, alkyl or O-alkyl,
iii. the compound of the formula II wherein R is —CH$_2$—CH=CH$_2$ and R$^1$ is H is converted into monoallyl compounds protected completely by R'CH$_2$—;
iv. these are converted stereoselectively by azidonitration into the azido-lactose derivatives of the

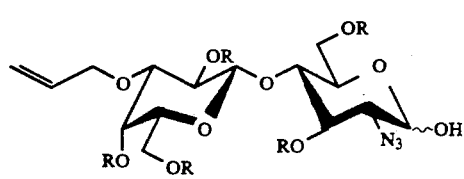

wherein R is R'CH$_2$—and R' has the meaning given;
v. the gluco-isomer of the compounds of the formula III is converted stereoselectively either into the azido-lactose derivatives of the formula IV

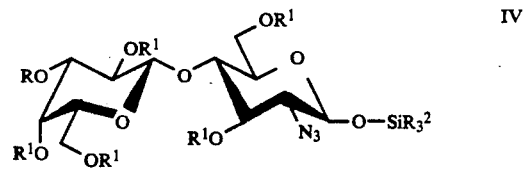

wherein the allyl compound initially formed is converted into the OH-free compound by splitting off the allyl group and the silyl radical has the β-configuration, or into activated azido-lactose derivatives of the formula V

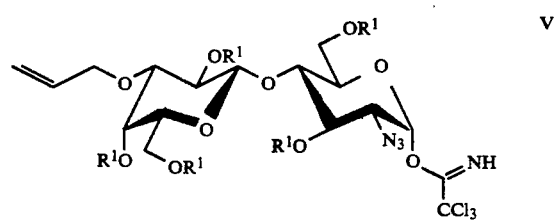

wherein the trichloroacetimidate radical (O—C(=NH)CCl$_3$) is preferably in the α-configuration, and wherein, in the formulae IV and V, R is R'CH$_2$—, R is allyl or H, R$^2$ is C$_1$ to C$_4$-alkyl or phenyl and R' has the meaning given;
vi. the disaccharides of the formula IV or V are converted, by introduction of a galactopyranosyl radical and substitution of the glycosidic radical of the glucopyranosyl ring by a spacer radical —O—S, into the compounds of the formula I
wherein
R is R'CH$_2$—, X is N$_3$ and S is a spacer, R' has the meaning given and the spacer radical has the β-configuration, and
vii. if appropriate, the azido group is reduced to —NHCOCH$_3$ and the OR radicals are reduced to OH groups.

The invention also relates to the new lactal derivatives of the formula II.

The invention furthermore relates to the new trisaccharides having the α(1–3),β(1–4)-configuration, of the formula VI

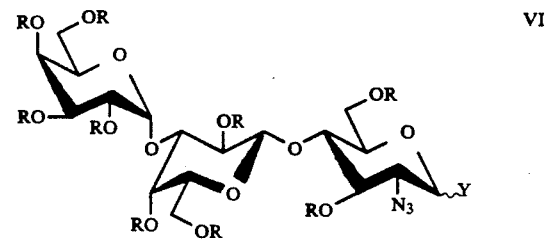

wherein R is R'CH$_2$—, Y is β-OSiR$^2$$_3$ or α-OC(NH)CCl$_3$ and R' and R$^2$ have the meanings given.

The invention furthermore relates to the new disaccharides having the β(1–4)-configuration, of the formula VII

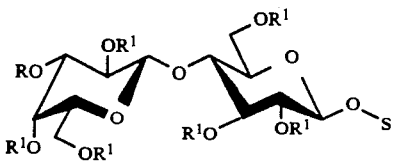

wherein S is a spacer of the formula —(CH$_2$)$_n$—COOR″, R″ is C$_1$ to C$_4$-alkyl, n is an integer from 4 to 12, R is allyl or H, R$^1$ is R′CH$_2$—and X is N$_3$ or —NHCOCH$_3$, and R′ has the meaning given.

Finally, the invention relates to the new β-linked oligolactosamines of the formula VIII

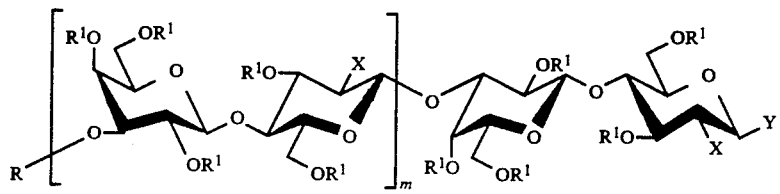

wherein
R is H or allyl,
R$^1$ is H or R′CH$_2$—,
X is N$_3$ or —NHCOCH$_3$,
Y is β-OSiR$^2$$_3$ or α—O—C(=NH)CCl$_3$,
R$^2$ is C$_1$ to C$_4$-alkyl or phenyl and
m is an integer from 1 to 4,
and R′ has the meaning given.

Compounds of the formula I are known per se (Garegg et. al. (1985), Carbohydrate Res. 136, 207-213). The trisaccharide components of these compounds are epitopes which are expressed on human tumor cells, while normal cells produce these epitopes only in very small amounts, if at all (for example Galili (1983), Lancet 2, 358-360) Such epitopes can accordingly function as a hapten and initiate antibodies which can be employed analogously as potential candidates for therapeutic treatment of tumors or tumor metastases such as leukemia, lymphoma, mamma carcinoma, ovarian carcinoma, gastrointestinal carcinoma, lung and bronchial carcinoma or for stimulation of the endogenous defense against tumor cells. The compounds have immunostimulating activity. (For example, Castronovo et. al. (1989), J. Natl. Cancer Inst. 81 (3), 212-216).

The preparation of the compounds of the formula I in which a spacer allows coupling to a protein matrix is thus a worthwhile aim in respect of their use in the medical sector. It has so far been possible to prepare a specific compound of the formula I (Garegg et. al.). However, the known synthesis proceeds via very many intermediate stages, which means it can be of only limited use for applications on an industrial scale. Because of the many intermediates stages, the total yield is, of course, not very high. On the other hand, such syntheses impose high stereoselectivity or stereospecificity requirements.

It has now been found that the compounds of the formula I can easily be prepared in an efficient, stereoselective and relatively short synthesis from commercially obtainable lactose if the synthesis leads via the partially alkylated glycals of the formula II, which have not hitherto been available, the double bond of the protected glycals is azidonitrated and, by introduction of the trichloroacetimidate or tert-butyldimethylsilyl group, which can easily be split off again, a corresponding donor or acceptor molecule is prepared, which reacts with a corresponding monosaccharide to give the desired compounds of the formula I or with the corresponding donor/acceptor disaccharide, under the action of preferably trimethylsilyl trifluoromethanesulfonate to give new β(1-3)-linked tetra- or oligolactosamines of the formula VIII. The latter are important determinants, which are likewise known as tumor antigens and can thus be employed in an analogous manner to the compounds of the formula I.

In particular, it has been found that the compounds of the formula II according to the invention can be prepared from D-lactal in particularly good yields under the action of dibutyltin oxide. It has furthermore been found that in addition to the compounds of the formula II, the compounds of the formulae VI and VII are also useful new intermediate products in the synthesis of the compounds of the formula I.

In addition to the excellent stereoselectivity, especially of some steps, the process according to the invention has only 15 synthesis steps, starting from lactose, in comparison with 23 synthesis steps when the process of Garegg et. al. is used.

The radicals R, R′, R$^1$, R″, X, Y and S above and below have the meanings given, unless expressly stated otherwise.

Depending on the formulae I to VIII, R and R′ are H, R′CH$_2$—, R′C(O)—or —CH$_2$—CHαCH$_2$; R′ is H or alkyl having 1 to 3 C atoms or phenyl which is unsubstituted or substituted by halogen, OH, alkyl or O-alkyl. If R′ is alkyl, these radicals are, specifically, methyl, ethyl, n-propyl or isopropyl.

In the case of R′CH$_2$—, R′ is preferably phenyl which is unsubstituted or substituted, but preferably unsubstituted. However, if R′ is substituted phenyl, the phenyl can be mono- or polysubstituted. With the exception of mesityl, however, it is preferably monosubstituted. Suitable substituents are F, Cl, Br, OH, alkyl having 1 to 3 C atoms or O-alkyl having 1 to 3 C atoms, but preferably F, OH or methyl.

In the case of R′C(O)—, R′ is preferably methyl or phenyl.

X is N$_3$ or —NHCOCH$_3$, but preferably —NHCOCH$_3$;

Y is β-OSiR$^2$$_3$ in the case of a (glycosyl) acceptor molecule or α—O—C(=NH)CCl$_3$ in the case of a (glycosyl) donor molecule.

R$^2$ is C$_1$ to C$_4$-alkyl or phenyl, it being possible for the radicals R$^2$ to be identical or different. However, —SiR$^3$$_3$ is preferably tert-butyldimethylsilyl (TBDMS) or texyldimethylsilyl (TDMS).

is a spacer radical —(CH$_2$)$_n$—COOR″, wherein R″ is C$_1$ to C$_4$-alkyl and n is an integer from 4 to 12. alkyl can be straight-chain or branched and is specifically methyl, ethyl, n-propyl, isopropyl, n-butyl, isobutyl or sec- or tert-butyl. R″ is preferably methyl or ethyl. n is preferably 6 to 10, but in particular 8. The particularly preferred spacer radical is —(CH$_2$)$_8$—COOEt. The spacer radical is bonded glycosidically to the di- or trisaccharide. It is preferably introduced as S—OH into the particular sugar radical. Bonding to a particular carrier protein molecule can take place via the COO-group of the spacer functioning as a distance-maintaining group. The hapten (sugar epitope) can display its antigenic or immunogenic action through this.

The process according to the invention is described in general form below. Process steps which correspond to standard methods of carbohydrate chemistry, such as, for example, the introduction and splitting off of suitable protective groups, are not explained in more detail. The standard literature is referred to in this respect (for example T. W. Greene, Protective Groups in Organic Synthesis, 1981, John Wiley & Sons; Methods in Carbohydrate Chemistry, Vol. I–VIII, Academic Press).

Lactose is first converted into D-lactal in a known manner (Kent et. al. (1977), J. Fluorine Chem. 10, 455-478). D-Lactal corresponds to a compound of the formula II in which all the radicals R' R$^1$ and R' are H. The use of the dibutyltin method (Wagner et. al. (1974), J. Org. Chem. 39, 24; Auge et. al. (1976), J. Chem. Soc. Chem. Commun., 375-376; and Nashed (1977), Carbohydr. Res. 56. 325-356), which is preferred in the process according to the invention, leads to compounds of the formula II in which only the radical R is alkylated, while the radicals OR$^1$ are present as free OH groups. Allyl substrates are preferably employed, so that the monoallylated compound of the formula II (R=—CH$_2$—CH=CH$_2$, R$^1$=H) is formed. The di-O-alkylated derivatives of the compounds of the formula II are formed as bi-products in small yields in this reaction. To determine the regiochemistry of the partial alkylation, the reaction products are peracetylated or treated with trichloroacetylisocyanate in a manner known per se and analyzed by means of NMR spectroscopy. For example, the preferred compound of the formula II (R=—CH$_2$—CH=CH$_2$, R$^1$=H) is obtained as a highly crystalline solid in a yield of 58 to 65% after chromatographic purification. The solvent used here can influence the content of bi-product. Higher yields of the di-O-allylated compound of the formula II are thus obtained if toluene is employed instead of benzene.

The formation of the mono- and dialkylated lactals of the formula II with the aid of the stannylation method is surprisingly in distinct contrast to the results of the alkylation of other glycals with the aid of the same method (Mereyala et. al. (1989), Carbohydr. Res. 187. 154-158).

The free OH groups of the compounds of the formula II are then alkylated or, preferably, benzylated. This is effected by standard methods, for example using alkyl(-benzyl)bromide in tetrahydrofuran. The completely protected lactals of the formula II are obtained in a virtually quantitative yields. The lactals of formula II are completely protected even where R$^1$ may be phenylsubstituted by a hydroxy group. The monoallylated lactal of the formula II is preferably employed.

The azidonitration of the completely protected compounds in a manner known per se (Lemieux et. al. (1979), Can. J. Chem. 57, 1244-1251). After the nitrate esters intermediately formed have been cleaved, the 1-OH-free azido-lactose derivatives of the formula III, preferably the corresponding monoallylated compounds, are obtained.

To prepare the acceptor unit IV, the preferably monoallylated compounds of the formula III are silylated on the anomeric OH group by standard methods, for example using tert-butyldimethylsilyl chloride (TBDMSCl).

The reaction leads stereoselectively to the β-silylated compounds, which are present in an epimer mixture (gluco/manno: 1.5 to 2.5:1). The epimer mixture can be separated and purified by chromatography, for example by means of medium pressure liquid chromatography (MPLC) by standard methods (for example Jung et. al. (1989), Liebigs Ann. Chem., 1099-1106). The epimers having the gluco-configuration are preferably suitable for the subsequent synthesis steps.

The allyl group of the silyl derivatives of the formula IV having the β-configuration is converted selectively into a free OH group, for example using Wilkinson's catalyst (Maranduba et. al. (1985), Carbohydr. Res. 135, 330) and with subsequent treatment with mercury(II) oxide/mercury(II) chloride to cleave the propenyl derivative intermediately formed. The lactosamine derivative of the formula IV in which R is H is thus preferentially obtained in an excellent yield.

The acceptor units of the formula IV obtainable as described are now reacted stereoselectively with per-O-benzylated or otherwise protected α-galactopyranosyl trichloroacetimidate, which is accessible from the literature (Wegmann et. al. (1987), J. Carbohydr. Chem. 6 (3), 357-375)-, preferably in the presence of trimethylsilyl trifluoromethanesulfonate, to give the new triaccharides having the α(1–3),β(1–4)-configuration, of the formula VI, wherein Y is —OSiR$^2$$_3$, but preferably —OTBDMS, and is in the B-configuration. The term "reacted stereoselectively" means a stereoselectivity of 95–100%, i.e., a nearly pure α/β configuration. The yield of α (1–3) β (1–4) configuration of formula VI is between 70 and 85%, preferably between 75 and 80%. Other customary Lewis acids, such as, for example, boron trifluoride diethyl ether, tin(II) chloride, zinc chloride, zinc chloride etherate, titanium tetrachloride or p-toluenesulfonic acid, are also suitable according to the invention in catalytic amounts. The stereoselective replacement of the glycosidic β-O-SiR$^2$$_3$ or β-O-TBDMS group by the trichloroacetimidate group having the α-configuration is effected by splitting off the acceptor group and forming the free 1-OH group by treatment with, preferably, tetrabutylammonium fluoride or other known acid agents which are suitable for this purpose, followed by reaction with trichloroacetonitrile under basic conditions, for example with the aid of sodium hydride or DBU, K$_2$CO$_3$ or CS$_2$CO$_3$. The new trichloroacetimidates, having the α-configuration, of the compounds of the formula VI are formed exclusively in this reaction in yields of between 70 and 80%.

The trichloroacetimidates of the compounds of the formula VI are reacted stereospecifically with the spacer reagent S—OH in the presence of a non-polar solvent, preferably a methylene chloride/n-hexane mixture, and a catalyst, preferably boron trifluoride diethyl ether, to give the β-glycosidically linked azido compounds of the formula I in good yields (70 to 80%).

The azido group can be reduced in a manner known per se, for example with sodium borohydride, and then acetylated with, for example, acetic anhydride (X=—NHCOCH$_3$). The hydrogenolytic dealkylation, in particular debenzylation, with, for example, palladium/carbon in preferably ethyl acetate/ethanol/water- /acetic acid leads finally to the compound of the formula I wherein R is H and X is —NHCOCH$_3$ and which can be employed in particular as a hapten.

In an alternative embodiment of the process according to the invention, the synthesis can also be continued with the aid of the compounds of the formula V. The compounds can be obtained from the compounds of the formula III by reaction with trichloroacetonitrile and sodium-hydride in a manner known per se. The α-trichloroacetimidates of the corresponding disaccharides are chiefly formed in this reaction.

As mentioned above, the resulting epimer mixture of gluco/manno derivatives can easily be separated. The subsequent course of the reaction is based on the gluco-isomers.

In this process variant, the spacer radical S is then already introduced by the procedure described above at the stage of the disaccharides. The new derivatives of the formula VII in which the spacer radical again is in the β-configuration are obtained.

The allyl group of the protected disaccharidespacer derivatives of the formula VII is then reduced to the free OH group, as described above. The compounds of the formula VII thus obtained are reacted with per-O-benzylated or otherwise protected α-galactopyranosyl trichloroacetimidate, as described above, to give the optionally dealkylated, —NHCOCH$_3$-substituted (on the original azido position) trisaccharides of the formula I. In addition to the compounds of the formula I, which have the α(1-3),β(1-4)-configuration and can be obtained in a yield of 60-70%, the corresponding trisaccharides having the β(1-3),β(1-4)-configuration are also formed to the extent of 16-20% in this process variant.

However, the process via the compounds of the formula IV is preferred, since on the one hand no trisaccharides having the β(1-3),β(1-4)-configuration, but exclusively the desired trisaccharides having the α(1-3),β(1-4)-configuration are formed, and on the other hand the yields of the reaction step relating to the coupling of the spacer radical are higher. The yield of the trisaccharide of formula I via the compounds of formula IV is between 75 and 90%, preferably between 80 and 85%.

The activated azido-lactose derivatives of the formula V and the lactosamine acceptor derivatives of the formula IV are important intermediate products in the stereoselective synthesis of new β(1-3)-linked oligolactosamines of the formula VIII. Such lactosamines can play an important role determinants on turmor antigens.

The compounds of the formula VIII can be prepared according to the invention by direct reaction of the compounds of the formula IV wherein R is H with those of the formula V in the presence of, preferably, trimethylsilyl trifluoromethanesulfonate, for example in a mixture of methylene chloride and n-hexane. In addition to trimethylsilyl trifluoromethanesulfonate, other abovementioned customary Lewis acids are also suitable in catalytic amounts. The β(1-3)-linked tetrasaccharides of the formula VIII wherein Y is β-O-TBDMS, R is allyl and m is 1 are initially formed exclusively in a yield of between 70 and 80%. Renewed deallylation and reaction with a further molecule of the formula V, as described above, gives the corresponding hexasaccharide (m=2). The corresponding oct- (m=3) and decasaccharide (m=4) can thus be prepared analogously. The utility of compounds of formula VIII is analogous to compounds of formula I.

Summarizing the process according to the invention for the preparation of the useful compounds of the formula I is distinguished by the following peculiarities.

the use of the stannylation method ensures the preparation of partially alkylated, protected new D-lactals, which are important intermediate products, in contrast to the analogous syntheses known to date;

the use of the trichloroacetimidate method allows an extremely high stereoselectivity of individual reaction steps;

in the preferred variant of the process according to the invention, the spacer is introduced into the molecule only in a late phase (in contrast to the immediate prior art according to Garegg et. al., yields and stereoselectivity can be improved in this way;

the process moreover allows easy access to new β(1-3) linked oligolactosamines which are useful for medicine.

The process according to the invention is illustrated with the aid of concrete examples below.

Chromatographic material used:

1. Thin layer chromatography: Silica gel 60 F-254 (E. Merck, Darmstadt, Germany), detection with 15% sulphuric acid.
2. Column chromatography: Silica gel 60, 0.063-0.200 nm (E. Merck, Darmstadt, Germany).
3. Medium pressure chromatography (MPLC): Silica gel LiChroPrep ® Si 60, 15-25 μm.
4. HPLC: Silica gel LC-8 (Shimadzu, Japan).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 41 19 472.1, filed Jun. 13, 1991, are hereby incorporated by reference.

EXAMPLES

Example 1

A mixture of D-lactal (600 mg, 1.94 mmol) and dibutyltin oxide (1.0 g, 4 mmol) in dry benzene is heated at the reflux temperature for about 20 hours. After the solution has been concentrated to about 20 ml, tetrabutylammonium iodide (700 mg, 2.0 mmol) and benzyl bromide (1 ml, 8.0 mmol) are added and the solution is boiled under reflux for about a further 3 hours. The solvent is stripped off under 10$^{-2}$ mmHg and the yellow residue is purified over a silica gel column (eluent: ethyl acetate/methanol 9:1). The fraction having an R$_F$ value of 0.39 is concentrated to dryness to give 400 mg (52%) of a colorless syrup, which crystallizes out from ethyl acetate.

4-O(3-O-Benzyl-β-D-galactopyranosyl)-D-arabino-hex-1-enitol, a compound of the formula II, is obtained.

R$_F$ value (TLC): 0.39 (ethyl acetate/methanol 9:1)
m.p.: 175° C.; [α]$_D$=+42.9 (c=1, chloroform).

Example 2

A mixture of D-lactal (308 mg, 1.0 mmol) and dibutyltin oxide (500 mg, 2.0 mmol) in dry toluene is heated at the reflux temperature for about 17 hours. After the solution has been concentrated to about 20 ml, tetrabutylammonium iodide (369 mg, 1.0 mmol) and benzyl bromide (0.5 ml, 4.0 mmol) are added and the solution is boiled under reflux for about a further 4 hours. The solvent is stripped off under $10^{-2}$ mmHg and the yellow residue is purified over a silica gel column (gradient eluent: ethyl acetate/methanol 1:0→9:1). The main fraction ($R_F$ value: 0.70, ethyl acetate/methanol 9:1) contains 180 mg (33%) of 4-O(3,6-di-O-benzyl-$\beta$-D-galactopyranosyl)-D-arabino-hex-1-enitol, a compound of the formula II. The smaller fraction which follows contains 90 mg (23%) of the compound prepared according to Example 1.

Example 3

A mixture of D-lactal (40 g, 0.130 mol) and dibutyltin oxide (64.6 g, 0.259 mol) in dry benzene (1100 ml) is heated at the reflux temperature for about 17 hours. To bring the reaction to completion, a molecular sieve (4 Å) is added and the mixture is boiled under reflux for a further 2 hours. When the solvent has been concentrated to about ⅓ of the volume, tetrabutylammonium iodide (47.8 g, 0.130 mol) and allyl bromide (31.4 g, 0.259 mol) are added to the batch. After 4 hours under reflux, no further reaction takes place (TLC: ethyl acetate/methanol 9:1). The solvent is stripped off and the residue is taken up in methylene chloride. The organic phase is extracted several times with water and the aqueous phase is concentrated. A yellow residue (69 g) is obtained and is purified by means of silica gel column chromatography (ethyl acetate/methanol 9:1). The fraction eluted first ($R_F$=0.67) contains the diallyl compound of the formula II, and in particular 4-O(3,6-di-O-allyl-$\beta$-D-galactopyranosyl)-D-arabino-hex-1-enitol (7 g, 12%). $[\alpha]_D = +40.9$ (c=1, chloroform).

The main fraction ($R_F$=0.31, 28 g, 60%) contains 4-O(3-O-allyl-$\beta$-D-galactopyranosyl)-D-arabino-hex-1-enitol, a compound of the formula II, which can be recrystallized from ethyl acetate. $R_F$ value (TLC): 0.45 (ethyl acetate/methanol 85:15) m.p.: 148°-149° C.; $[\alpha]_D = +41.3$ (c=1, chloroform).

Example 4

Sodium hydride (6×1.65 g, 69 mmol) and benzyl bromide (6×10.2 ml, 86 mmol) are added in portions to a suspension of the monoallyl derivative prepared according to Example 3 (12.0 g, 34.4 mmol) in dry tetrahydrofuran, while stirring vigorously. The mixture is heated to the reflux temperature and catalytic amounts of tetrabutylammonium iodide and 18-crown ether-6 are added. After about 19 hours at 60° C. under controlled release of hydrogen, the reaction stops (checking of the reaction by TLC). The mixture is cooled to room temperature and filtered. Crushed ice is added to the filtrate and the solution is extracted several times with diethyl ether. The organic phase is neutralized, washed several times with sodium chloride solution, dried over magnesium sulfate and evaporated. The residue is purified over silica gel (eluent: petroleum ether then ethyl acetate) to remove liquid by-products, and finally purified further by means of flash chromatography (petroleum ether/ethyl acetate 85:15). 26 g (95%) of 3,6-di-O-benzyl-4-O(2,4,6-tri-O-benzyl-3-O-allyl-$\beta$-D-galactopyranosyl)-D-arabino-hex-1-enitol, a compound of the formula II, are obtained as a yellow syrup. $R_F$ value (TLC): 0.40 (petroleum ether/ethyl acetate 8:2); $[\alpha]_D = -13.8$ (c=1, chloroform).

Example 5

A solution of the compound prepared in Example 4 (4.0 g, 5 mmol) in dry acetonitrile (60 ml) is cooled to −30° C. under an argon gas atmosphere. Cerium ammonium nitrate (6.85 g, 12.5 mmol) and sodium azide (0.41 g, 6.26 mmol) are added, while stirring vigorously. After about 17 hours at −30° C. and a further 3 hours at −20° C., the suspension is filtered, the residue is extracted by shaking with diethyl ether and, after addition of ice to the filtrate, the organic phase is washed several times with salt solution until neutral. After the solvent has been evaporated off at a low temperature, a yellow residue is obtained, which is purified over silica gel using petroleum ether/ethyl acetate (8:2) to give, after the solvent has been stripped off, a pale yellow syrup of an isomer mixture of the intermediately formed azidonitrates of the compounds of the formula III. This mixture (17.8 g, 19.7 mmol) is dissolved in 200 ml of dioxane and a solution of sodium nitrite (17.8 g) in 70 ml of water is added. The mixture is stirred vigorously at 85° C. After 7 to 8 hours, the reaction stops (checking by TLC). The mixture is poured onto ice and extracted with diethyl ether. The organic phase is washed neutral with water, dried over magnesium sulfate and evaporated and the residue is purified by means of flash chromatography (petroleum ether/ethyl acetate 3:1). 8.6 g (51%) of 2-azido-3,6-di-O-benzyl-4)(3)-allyl-2,4,6-tri-O-benzyl-$\beta$-D-galactopyranosyl)-2-deoxy-$\beta$-D-glucopyranose, a compound of the formula III, are obtained as a yellow syrup. $R_F$ value (TLC): 0.18 (petroleum ether/ethyl acetate 3:1); $[\alpha]_D = +10.8$ (c=1, chloroform).

Example 6

Imidazole (800 mg, 11.7 mmol) and tert-butyldimethylsilyl chloride (1.53 g, 10.2 mmol) are added to a solution of the compound prepared in Example 5 (6.7 g, 7.8 mmol) in dry dimethylformamide. The solution is stirred at room temperature for about 18 hours. Tert-Butyldimethylsilyl trifluoromethanesulfonate (2.06 g, 7.8 mmol) and renewed imidazole (800 mg, 11.7 mmol) are added to the reaction batch to react the starting material still present and the mixture is stirred at 60° C. for a further 18 hours. It is then concentrated, the residue is diluted with methylene chloride and the mixture is washed several times with cold water, dried over sodium sulphate and concentrated again. The crude product is purified by chromatography over silica gel (petroleum ether/ethyl acetate 3:1) and the epimer mixture (gluco/manno) is separated by means of flash chromatography-(petroleum ether/ethyl acetate 9:1). tert-Butyldimethylsilyl 4O-(3O-allyl 2,4,6-tri-O-benzyl-$\beta$-D-galactopyranosyl)-2-azido-3,6-di-O-benzyl-2-deoxy-$\beta$-D-glucopyranoside, a compound of the formula IV, is obtained as a colorless viscous liquid (3.5 g, 46%). $R_F$ value (TLC): 0.20 (petroleum ether/ethyl acetate 9:1); $[\alpha]_D = -17.2$ (c=1, chloroform).

Example 7

Tris(triphenylphosphine)-rhodium(I) chloride (0.69 g, 0.75 mmol) is added to a solution of the compound prepared in Example 6 (4.9 g, 5.0 mmol) in ethanol/- toluene/water (360 ml, 8:3:1) and the mixture is heated under reflux for 2 hours. The slightly yellow solution is concentrated, the residue is diluted with 300 ml of methylene chloride and the organic solution is washed neutral and evaporated. The residue is taken up in acetone/water (200 ml, 10:1), and HgO (162 mg, 0.75 mmol) and HgCl$_2$ (6.8 g, 25.0 mmol) are added. The mixture is stirred at room temperature for 1 hour. The solvent is then stripped off and the residue is taken up in 400 ml of methylene chloride. The organic phase is washed several times with water, aqueous potassium iodide solution and again with water until neutral, dried over magnesium sulfate and evaporated. The brown residue is purified by means of flash chromatography (petroleum ether/ethyl acetate 8:2). tert-Butyldimethy)silyl 2-azido-3,6-di-O-benzyl-(2,4,6-tri-O-benzyl-$\beta$-D-galactopyranosyl)-2-deoxy-$\beta$-D-glucopyranoside, a compound of the formula IV, is obtained as a syrup (4.0 g, 86%). R$_F$ value (TLC): 0.50 (petroleum ether/ethyl acetate 3:1); [$\alpha$]$_D$= −18.6 (c=1, chloroform).

Example 8

A solution of trimethylsilyl trifluoromethanesulfonate (0.1 M, 0.5 ml diluted with 1 ml of diethyl ether) is added dropwise to the carefully dried compound prepared according to Example 7 (2.06 g, 2.21 mmol) and $\alpha$-galactopyranosyl trichloroacetimidate (3.025 g, 4.415 mmol) in dry diethyl ether (44 ml) at −20° C. under an argon inert gas atmosphere. After 5 hours, solid sodium bicarbonate is added and the mixture is filtered and evaporated. The residue is purified by means of flash chromatography (petroleum ether/ethyl acetate 8:2). tert-Butyldimethylsilyl O-(2,3,4,6-tetra-O-benzyl-$\beta$-D-galactopyranosyl)-(1→3)-O-(2,4,6-tri-O-benzyl-$\beta$-D-galactopyranosyl)-(1→4)-O-2-azido-3,6-di-O-benzyl-2-deoxy-$\beta$-D-glucopyranoside, a compound of the formula VI, is obtained as a syrup (2.4 g, 75%). R$_F$ value (TLC): 0.23 (petroleum ether/ethyl acetate 6:4); [$\alpha$]$_D$= +17.5 (c=1, chloroform).

Example 9

A solution of tetrabutylammonium fluoride (0.1M, 2.5 ml diluted with 5 ml of tetrahydrofuran) is added dropwise to the carefully dried compound prepared according to Example 8 (1.82 g, 1.25 mmol) in dry tetrahydrofuran (40 ml) at −20° C. under argon. After 2 hours, the mixture is poured onto ice and extracted intensively with diethyl ether. The organic phase is washed with salt solution and with water until neutral, dried over magnesium sulfate and concentrated and the residue is chromatographed (petroleum ether/ethyl acetate 7:3). The resulting dried yellow syrup (1.4 g, 1.05 mmol) is taken up in dry methylene chloride (35 ml), and trichloroacetonitrile (1.5 ml, 15.8 mmol) and sodium hydride (10×25 mg, 1.05 mmol) are added under argon. The suspension is stirred at room temperature for 5 hours, filtered and concentrated and the residue is purified by means of flash chromatography (petroleum ether/ethyl acetate 8:2). O-(2,3,4,6-tetra-O-benzyl-$\alpha$-D-galactopyranosyl)-(1.3)-O-(2,4,-tri-O-benzyl-$\beta$-D-galactopyranosyl) -(1→4)-O-2-azido-3,6-di-O-benzyl-2-deoxy-$\beta$-D-glucopyranosyl trichloroacetimidate, a compound of the formula VI, is obtained as a yellow syrup (1.1 g, 70%). R$_F$ value (TLC) 0.48 (petroleum ether/ethyl acetate 7:3); [$\alpha$]$_D$= −30.0 (c=1, chloroform).

Example 10

A solution of boron trifluoride/diethyl ether (0.1M, 16.5 ml in 3 ml of methylene chloride/n-hexane 1:2) is added to a solution of the thoroughly dried compound prepared according to Example 9 (2.93 g, 1.97 mmol) and 8-ethoxy-carbonyloctanol (800 mg, 4.0 mmol) in methylene chloride/n-hexane (36 ml, 1:1) at -15° C. under argon. After about 5 hours, the solution is neutralized by addition of sodium bicarbonate, filtered and evaporated in vacuo and the residue is chromatographed as described (petroleum ether/diethyl ether 6:4). 8-Ethoxycarbonyloct-1-yl-O-(2,3,4,6 tetra-O-benzyl-$\alpha$-D-galactopyranosyl)-(1→3)-O-(2,4,6-tri-O-benzyl-$\beta$-D-galactopyranosyl)-(1→4)-O-2-azido-3,6-di-O-benzyl-2-deoxy-$\beta$-D-glucopyranoside, a compound of the formula I, is obtained as a syrup (2.6 g, 85%).

Example 11

A saturated solution of sodium borohydride in ethanol is added dropwise to a mixture of the compound prepared according to Example 10 (246 mg, 0.16 mmol) in dioxane (2 ml) and 50 ml of a solution of 4% of NiCl$_2$×6H$_2$O and 2% of H$_3$BO$_3$ in ethanol, until no further starting material is present (about 8 hours). Acetic anhydride (1.5 ml) is then added and the mixture is stirred at 4° C. for a further 2 days. The suspension is diluted with ice-water and extracted several times with methylene chloride. The combined extracts are washed with saturated sodium bicarbonate solution and water until neutral, dried over magnesium sulfate and evaporated in vacuo. After purification by MPLC (eluent: petroleum ether/ethyl acetate 6:4), 242 mg (100%) of a syrup of 8-ethoxycarbonyloct-1-yl-O-(2,3,4,6-tetra-O-benzyl-$\alpha$-D-galactopyranosyl)-(1→3)-O-(2,4,6-tri-O-benzyl-$\beta$-D-galactopyranosyl)-(1→4)-O-2-acetamido-3,6-di-O-benzyl-2- deoxy-$\beta$-D-glucopyranoside, a compound of the formula I, are obtained. R$_F$ value (TLC): 0.28 (petroleum ether/ethyl acetate 6:4).

Example 12

Catalytic amounts of Pd/C are added to a solution of the compound prepared according to Example 11 (83 mg, 54 $\mu$mol) in ethyl acetate/ethanol/water/acetic acid (11 ml, 7:3:1:0.05) and the mixture is reduced with hydrogen. After about 12 hours, the reaction has ended and the mixture is filtered, concentrated in vacuo and purified by means of MPLC (methylene chloride/methanol 1:1). After the solvent has been stripped off, 8-ethoxycarbonyloct-1-yl-O-$\alpha$-D-galactopyranosyl-(1→3)-$\beta$-D-galactopyranosyl-(1→4)-O-2-acetamido-2 deoxy-$\beta$-D-glucopyranoside, a compound of the formula I, is obtained as an amorphous material (30 mg, 77%); R$_F$ value (TLC): 0.16 (ethyl acetate/methanol/water 8:2:1).

Example 13

Trichloroacetonitrile (0.58 ml, 5.8 mmol) and sodium hydride 6.33 13.9 mg, 0.58 mmol) are added to a solution of the compound prepared in Example 5 (500 mg, 0.58 mmol) in dry methylene chloride (20 ml) under argon. After stirring at room temperature for about 6 hours, the suspension is filtered and concentrated and the residue is filtered over SiO$_2$ (petroleum ether/ethyl acetate 6:4). The epimer mixture formed (gluco/manno) is purified by means of MPLC (petroleum ether/diethyl ether 3:2). 280 mg (48%) of O-[4-O-(3-O-allyl-2,4,6-tri-O-benzyl-$\beta$-D-galactopyranosyl)-2-azido-3,6-di-O-benzyl-2-deoxy-β-D-glucopyranosyl]trichloroacetimidate, a compound of the formula V, are obtained; m.p.: 66°–67° C.; $R_F$ value (TLC): 0.51 (petroleum ether/ethyl acetate 3:2);

$[\alpha]_D = +27.1$ (C=1, chloroform).

Example 14

A solution of boron trifluoride/diethyl ether (0.1M) in methylene chloride (0.5 ml in 2 ml of n-hexane) is added to a solution of the compound prepared in Example 13 (200 mg, 0.20 mmol) and 8-ethoxycarbonyloctanol (98 mg, 0.20 mmol) in methylene chloride/n-hexane (10 ml, 1:4) at −20° C. under argon. After 3 hours, the solution is neutralized by addition of solid sodium bicarbonate, filtered and evaporated in vacuo. The residue is purified by filtration over SiO2 and by means of MPLC (petroleum ether/ethyl acetate 4:1). 8-Ethoxycarbonyloct-1-yl O-2-azido-3,6-di-O-benzyl-4-O-(3-O-allyl-2,4,6-tri-O-benzyl-β-D-galactopyranosyl)-2-deoxy-β-D-glucopyranoside, a compound of the formula VII, is obtained in a pure form (115 mg, 55%);

$R_F$ value (TLC): 0.32 (petroleum ether/ethyl acetate 4:1); $[\alpha]_D = -14.8$ (c=1, chloroform).

Example 15

The compound prepared according to Example 14 (535 mg, 0.513 mmol) is dissolved in toluene/ethanol/water (30 ml, 3:8:2), and tris(triphenylphosphine)-rhodium(I) chloride (72 mg, 0.08 mmol) is added to the solution. After about three hours under reflux, no further starting material is present. The mixture is evaporated, the residue is taken up in methylene chloride, the mixture is washed with water and evaporated again and the residue is dissolved in acetone/water (20 ml, 10:1). HgO (17 mg, 0.078 mmol) and HgCl2 (706 mg, 2.60 mmol) are then added. After one hour at room temperature, the mixture is concentrated, the residue is diluted with methylene chloride and the organic phase is washed with water and potassium iodide solution, dried and concentrated. The residue is purified by means of flash chromatography (petroleum ether/ethyl acetate 8:2). 8-Ethoxycarbonyloct-1-yl O-2-azido-3,6 di-O-benzyl-4-O-(4,6-tri-O-benzyl-β-D-galactopyranosyl)-2-deoxy β-D-galactopyranosyl)-2-deoxy-β-D-glucopyranoside, a compound of the formula VII, is obtained as a viscous liquid (455 mg, 89%); $R_F$ value (TLC): 0.43 (petroleum ether/ethyl acetate 7:3); $[\alpha]_D = -17.7$ (c=1, chloroform).

Example 16

A solution of trimethylsilyl trifluoromethanesulfonate (0.1M, 0.2 ml diluted with 1 ml of diethyl ether) is added dropwise to a solution of the compound prepared according to Example 15 (141 mg, 0.141 mmol) and α-galactopyranosyl trichloroacetimidate (116 mg, 0.17 mmol) in dry diethyl ether (3 ml) at room temperature under an argon atmosphere. After 3 hours, solid sodium bicarbonate is added and the mixture is filtered and concentrated. The residue is purified by means of MPLC (petroleum ether/diethyl ether 1:1). A mixture (170 mg, 79%) of 8-ethoxycarbonyloct-1-yl O-(2,3,4,6-tetra-O-benzyl-α-D-galactopyranosyl)-(1→3)-O-(2,4,6-tri-O-benzyl-β-D-galactopyranosyl)-(1→4)-O-(2-azido-3,6-di-O-benzyl-2-deoxy-β-D-glucopyranoside), a compound of the formula I, and 8-ethoxycarbonyloct-1-yl O-(2,3,4,6-tetra-O-benzyl-α-D-galactopyranosyl)-(1→3)-O-(2,4,6-tri-O-benzyl-β-D-galactopyranosyl)-(1→4)-O-(2-azido-3,6-di-O-benzyl-2-deoxy-β-D-glucopyranoside) is obtained.

The isomers can be separated by renewed MPLC. The corresponding α-isomer is obtained in an amount of 61% and the corresponding undesired β-isomer in an amount of 17%.

$R_F$ value (TLC) α-isomer: 0.21 (petroleum ether/ethyl acetate 6:4)

$R_F$ value (TLC) β-isomer: 0.28 (petroleum ether/ethyl acetate 6:4).

Example 17

A solution consisting of a donor compound prepared according to Example 13 (200 mg, 0.20 mmol) and an acceptor compound prepared according to Example 7 (186 mg, 0.20 mmol) in a little methylene chloride (about 3 ml) is cooled to −20° C. under argon, and n-hexane (8 ml) is added. The reaction is started by dropwise addition of a solution of trimethylsilyl trifluoromethanesulfonate (0.1M, methylene chloride) in n-hexane. After about one hour, the solution is washed, neutralized, filtered and concentrated as described in the other examples. The residue is filtered over silica gel and purified further by means of MPLC (petroleum ether/ethyl acetate 8:2). After the solvent has been evaporated off, tert-butyldimethylsilyl O-(3→4)-allyl-2,4,6-tri-O-benzyl-β-D-galactopyranosyl)-(143 4)-O-(2-azido-3,6-di-O-benzyl-2-deoxy-β-D-glucopyranosyl)-(1→3)-O-(2,4,6-tri-O-benzyl-β-D-galactopyranosyl)-(1→4)-O-(2-azido-3,6-di-O-benzyl-2-deoxy-β-D-glucopyranoside), a compound of the formula VIII, is obtained as a syrup (255 mg, 72%);

$R_F$ value (TLC): 0.37 (petroleum ether/ethyl acetate 8:2); $[\alpha]_D = -33.5$ (c=1, chloroform).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the stereoselective preparation of a trisaccharide having α(1-3),β(1-4)-configuration, of formula I

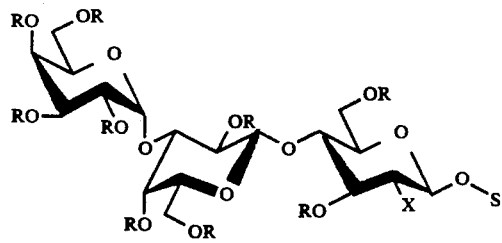

wherein

R is H or R'CH2—,

R' is H or $C_{1-3}$-alkyl or phenyl which is optionally substituted by halogen, OH, alkyl or O-alkyl, S is a spacer wherein S is —(CH2)n—COOR", R" is $C_1$ to $C_4$-alkyl and n is an integer from 4 to 12, X is $N_3$ or —NHCOCH3, from lactose, comprising i. converting lactose into D-lactal;
ii. partially alkylating D-lactal to give a lactal derivative of formula II

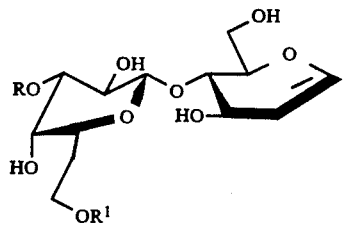

wherein
R is R'CH$_2$-or —CH$_2$—CH=CH$_2$,
R$^1$ is H, R'CH$_2$—, —CH$_2$—CH=CH$_2$ or R'—C(O)— —and
R' is H, C$_{1-3}$-alkyl or phenyl optionally substituted by halogen, OH, alkyl or O-alkyl;

iii. converting the compound of the formula II, wherein R is —CH$_2$—CH=CH$_2$ and R$^1$ is H into monoallyl compounds protected completely by R'CH$_2$—;

iv. converting the monoallyl compound stereoselectively by azidonitration into the azido-lactose derivatives of the formula III

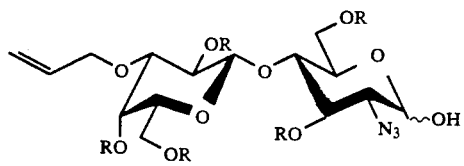

wherein R is R'CH$_2$—and R' has the meaning given;
v. converting stereoselectively the compounds of the formula III either into the azido-lactose derivatives of the formula IV

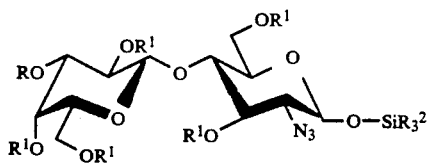

wherein the allyl compound initially formed is converted into the OH-free compound by splitting off the allyl group and the silyl radical has the $\beta$-configuration, or into activated azido-lactose derivatives of the formula V

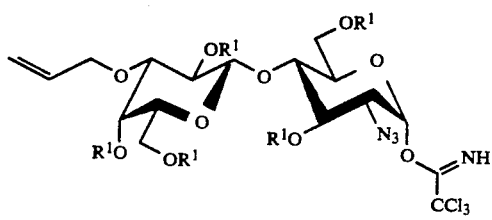

wherein the trichloroacetimidate radical (O—C(=NH)CCl$_3$) is in the $\alpha$-configuration, and wherein, in the formulae IV and V, R$^1$ is R'CH$_2$—, R is allyl or H, R$^2$ is C$_1$ to C$_4$-alkyl or phenyl and R' has the meaning given;

vi. converting the disaccharides of the formula IV or V by introduction of a galactopyranosyl ring by a spacer radical —O—S, into the compounds of the formula I
wherein
R is R'CH$_2$—, X is N$_3$ and S is a spacer, and
R' has the meanings given and the spacer radical has the $\beta$-configuration.

2. A process according to claim 1, wherein process step ii is carried out in the presence of dibutyltin oxide.

3. A process according to claim 1, wherein in process step vi, the disaccharides of the formula IV are reacted stereoselectively with $\alpha$-galactopyranosyl trichloroacetimidate to give the compounds having the $\alpha$(1-3),$\beta$(1-4)-configuration, of the formula VI

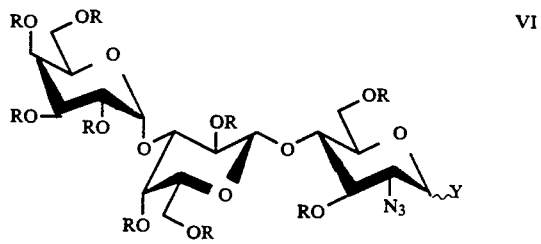

and then the O-silyl group initially present in the $\beta$-position is replaced by the OC(=NH)CCl$_3$ group in the $\alpha$-position, and the compounds thus obtained are reacted with a spacer reagent to give the compounds of the formula I, wherein, in the formula VI, R is R'CH$_2$—, Y is $\beta$-OSiR$^2_3$ or $\alpha$-OC(=NH)CCl$_3$ and R' and R$^2$ have the meanings given.

4. A process according to claim 1, wherein in process step vi, the disaccharides of the formula V are reacted with a spacer reagent to give compounds of the formula VII

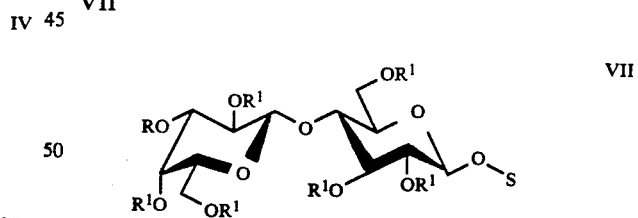

wherein R$^1$ is R'CH$_2$—m R is allyl or H, X is N$_3$ or —NHCOCH$_3$, S is a spacer and R' has the meaning given, the protection of the allyl compound initially formed being removed by splitting off of the allyl protective group to give the OH-free compound, and this compound being reacted with $\alpha$-galactopyranosyl trichloroacetimidate to give the compounds of the formula I.

5. A process according to claim 1, wherein a compound of the formula S—OH is employed as the spacer reagent, wherein S is —(CH$_2$)$_n$—COOR'', R'' is C$_1$ to C$_4$-alkyl and n is an integer from 4 to 12.

6. A process for the stereoselective preparation of the compounds of the formula VIII

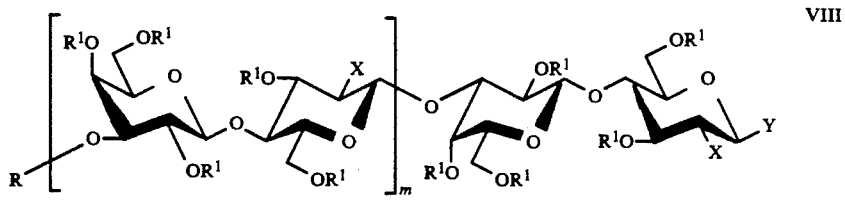

wherein
 R is H or allyl,
 $R^1$ is H or $R'CH_2-$,
 X is $N_3$ or $-NHCOCH_3$,
 Y is $\beta$-$OSiR^2_3$ or $\alpha$-$O$-$C(=NH)CCl_3$,
 $R^2$ is $C_1$ to $C_4$-alkyl or phenyl and
 m is an integer from 1 to 4,
 and R' has the meaning given,
 wherein process steps i–v are carried out according to claim 1 and a compound of the formula IV wherein R is H is reacted with a compound of the formula V in the presence of a Lewis acid to give a tetrasaccharide of the formula VIII (m=1).

7. A process according to claim 6, wherein the Lewis acid is trimethylsilyl trifluoromethanesulfonate.

8. A process according to claim 6, wherein the tetrasaccharide of formula VIII is reacted with one or more compounds of the formula V in the presence of a Lewis acid to obtain the corresponding oligosaccharide (M≦1).

9. A process according to claim 1, wherein the azido group is reduced to $-NHCOCH_3$ and the OR radicals are reduced to OH groups.

10. A process according to claim 1, wherein $R^1$ is methyl, ethyl, n-propyl or isopropyl.

11. A process according to claim 1, wherein $R^1$ is unsubstituted phenyl.

12. A process according to claim 1, wherein S is $-(CH_2)_8-COOEt$.

13. A process according to claim 1, wherein X is $NHCOCH_3$.

14. A process according to claim 1, wherein the monoallylated compound of formula III is silylated using tertiary butyl dimethyl silyl chloride.

15. A process according to claim 1, wherein the compound of formula I is substantially $\alpha(1,3),\beta(1-4)$-configuration.

* * * * *